United States Patent
Sumanaweera et al.

(10) Patent No.: US 6,503,204 B1
(45) Date of Patent: Jan. 7, 2003

(54) TWO-DIMENSIONAL ULTRASONIC TRANSDUCER ARRAY HAVING TRANSDUCER ELEMENTS IN A NON-RECTANGULAR OR HEXAGONAL GRID FOR MEDICAL DIAGNOSTIC ULTRASONIC IMAGING AND ULTRASOUND IMAGING SYSTEM USING SAME

(75) Inventors: Thilaka S. Sumanaweera, San Jose, CA (US); William Dreschel, State College, PA (US)

(73) Assignee: Acuson Corporation, Mountain View, CA (US)

( * ) Notice: Subject to any disclaimer, the term of this patent is extended or adjusted under 35 U.S.C. 154(b) by 0 days.

(21) Appl. No.: 09/540,384

(22) Filed: Mar. 31, 2000

(51) Int. Cl.$^7$ .................................................. A61B 8/00
(52) U.S. Cl. ...................................... 600/459; 29/25.35
(58) Field of Search .................... 600/437, 440–441, 600/443, 447, 459; 73/625–626

(56) References Cited

U.S. PATENT DOCUMENTS

| | | |
|---|---|---|
| 5,164,920 A | 11/1992 | Bast et al. |
| 5,295,487 A * | 3/1994 | Saitoh et al. ................ 600/459 |
| 5,537,367 A * | 7/1996 | Lockwood et al. ............ 367/87 |
| 5,546,946 A * | 8/1996 | Souquet ........................ 600/459 |
| 5,579,768 A * | 12/1996 | Klesenski ..................... 73/631 |
| 5,793,701 A | 8/1998 | Wright et al. |
| 5,808,962 A | 9/1998 | Steinberg et al. |
| 5,893,832 A * | 4/1999 | Song ............................ 600/443 |
| 5,995,453 A * | 11/1999 | Hirata ......................... 367/155 |
| 6,014,897 A * | 1/2000 | Mo .............................. 73/628 |
| 6,102,857 A * | 8/2000 | Kruger ......................... 600/437 |
| 6,102,860 A * | 8/2000 | Mooney ....................... 600/443 |

OTHER PUBLICATIONS

Shelby S. Brunke et al., *Broad–Bandwidth Radiation Patterns of Sparse Two–Dimensional Vernier Arrays;* Sep. 1997; pp. 1101–1109.

Richard E. Davidsen et al; *Two–Dimensional Random Arrays for Real Time Volumetric Imaging;* 1994; pp. 143–163.

Andrew Cittadine, Sensant Corp.; *Mems Reshapes Ultrasonic Sensing;* Feb. 2000; pp. 17–26.

* cited by examiner

Primary Examiner—Francis J. Jaworski

(57) ABSTRACT

Two-dimensional transducer arrays used for one-, two- and three-dimensional medical diagnostic ultrasonic imaging. The transducer arrays have transducer elements that are arranged in a non-rectangular, and preferably hexagonal grid. In a preferred embodiment, the transducer array has hexagonally shaped transducer elements. The transducer arrays may be fabricated as single or multiple layer structures. Sparse transducer arrays may be fabricated in a hexagonal grid by connecting selected transducer elements to the imaging system. Also, the transducer array may comprise random, vernier and spiral arrays fabricated in a hexagonal grid.

22 Claims, 2 Drawing Sheets

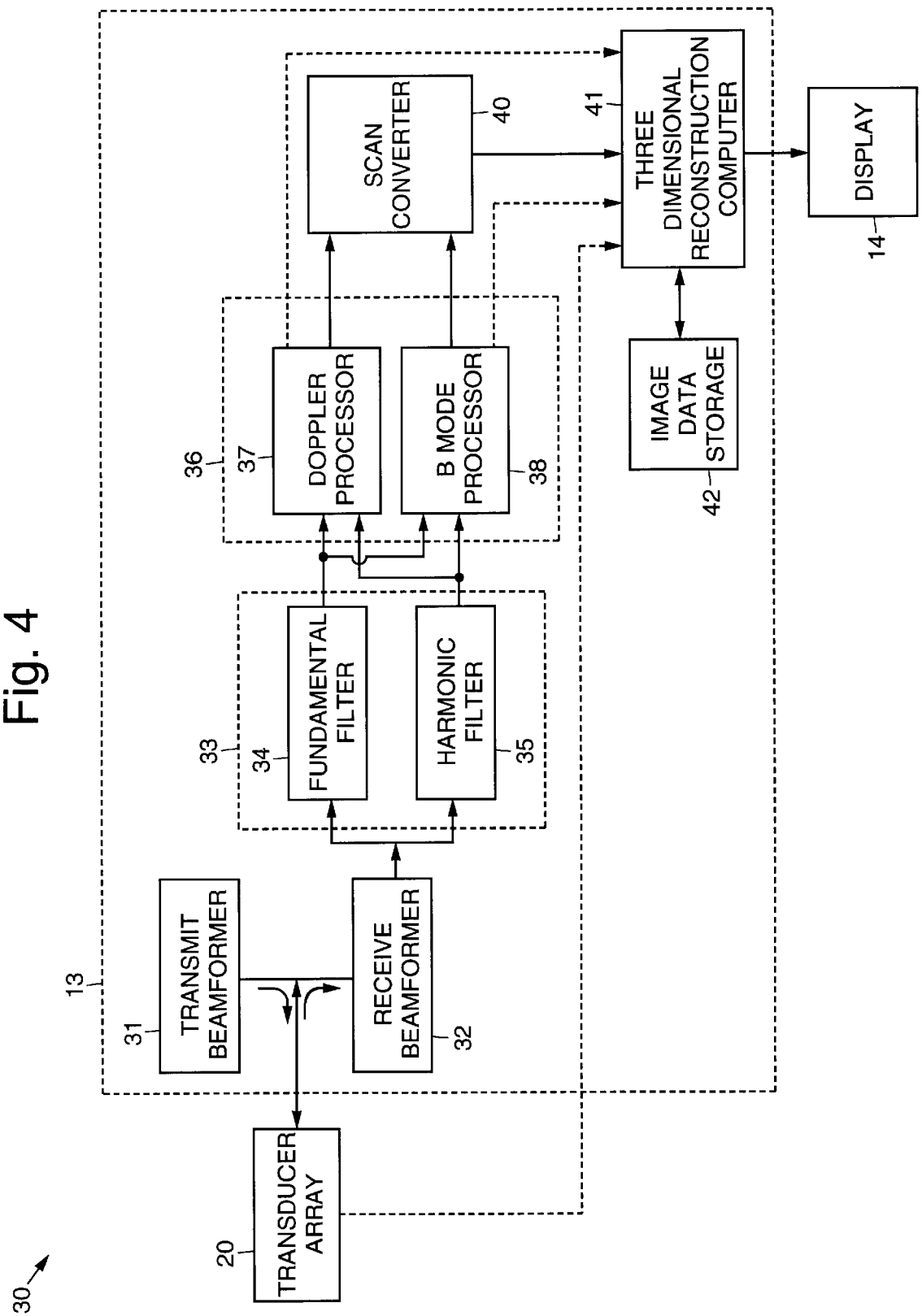

TWO-DIMENSIONAL ULTRASONIC TRANSDUCER ARRAY HAVING TRANSDUCER ELEMENTS IN A NON-RECTANGULAR OR HEXAGONAL GRID FOR MEDICAL DIAGNOSTIC ULTRASONIC IMAGING AND ULTRASOUND IMAGING SYSTEM USING SAME

BACKGROUND OF THE INVENTION

The present invention relates generally to ultrasonic transducer arrays for use in ultrasound imaging systems, and more particularly, to two-dimensional ultrasonic transducer arrays used for medical diagnostic ultrasonic imaging having transducer elements arranged in a non-rectangular or hexagonal grid, and ultrasound imaging systems employing same. Heretofore, ultrasonic transducer arrays have been manufactured having transducer elements fabricated and arranged in a rectangular grid. Such conventional transducer arrays are relatively costly because of a relatively high element count. Also, the elements of the conventional transducer arrays are not symmetrical such that they maximize the two-dimensional symmetry of the point spread function.

In the case of fully populated arrays, all of the transducer elements are connected to an ultrasound system. In the case of sparse (sparsely-populated) arrays, only some of the elements are connected to the ultrasound system. Sparse arrays include random arrays, vernier arrays and spiral arrays.

Conventional sparse arrays are described in the following references: R. E. Davidsen, J. A. Jensen, and S. W. Smith, "Two-dimensional random arrays for real time volumetric imaging", Ultrasonic Imaging, vol. 16, pp. 143–163,1994, S. S. Brunke and G. R. Lockwood, entitled "Broad-Bandwidth Radiation Patterns of Sparse Two-Dimensional Vernier Arrays," IEEE Transactions on Ultrasonics, Ferroelectrics and Frequency Control, vol. 44, no. 5, pp. 1101–1109,1997, U.S. Pat. No. 5,808,962, issued Sep. 15, 1998, entitled "Ultrasparse, ultrawideband arrays", and U.S. Pat. No. 5,537,367 issued Jul. 16, 1996, entitled "Sparse Array Structures".

U.S. Pat. No. 5,164,920 entitled "Composite ultrasound transducer and method for manufacturing a structured component therefore of piezoelectric ceramic" discloses a composite ultrasound transducer array containing piezoelectric ceramic transducer elements which radiate substantially in the longitudinal direction, and are embedded in a polymer matrix. The transducer elements have a geometrical structure, and are arranged relative to each other, so that development of oscillation modes perpendicular to the longitudinal direction of the transducer elements is suppressed. The transducer elements may have an arbitrary shape and arrangement, such as hexagonal or irregular square structures, having a trapezoidal cross-section in planes parallel to the longitudinal axis of the transducer elements.

However, there is no disclosure or suggestion in U.S. Pat. No. 5,164,920 regarding a transducer whose elements are arranged in a hexagonal grid, only hexagonal piezoelectric transducer elements are disclosed. U.S. Pat. No. 5,164,920 also discloses the use of structured electrodes that cover multiple ones of the hexagonal piezoelectric transducer elements, thus. defining transmission elements that are not necessarily hexagonal. In particular it is stated that the "structured electrode 24 may be annular or linear" and that "Using the structured electrode 24, predetermined transducer elements 22 are combined into separately drivable groups". None of the above-cited prior art references disclose a two-dimensional transducer having hexagonal elements with each hexagonal element having its own electrode.

Therefore, it would be desirable to distribute transducer elements of a two-dimensional transducer array so that the element count is minimized and thus minimize the cost of the circuitry. It would also be desirable to distribute the transducer elements so that the two-dimensional symmetry of the point spread function is maximized. This is important because in medical diagnostic ultrasonic imaging, the transducer array is coupled to an ultrasound imaging system that must produce symmetric speckle shapes. It would also be desirable to have a two-dimensional transducer array having hexagonally shaped elements that each has its own electrode. It would also be desirable to have improved ultrasound imaging systems that may used for medical diagnostic ultrasonic imaging that employ two-dimensional ultrasonic transducer arrays having transducer elements arranged in a non-rectangular or hexagonal grid.

BRIEF SUMMARY OF THE INVENTION

The present invention provides for two-dimensional transducer arrays used for one-, two- and three-dimensional medical diagnostic ultrasonic imaging. The present two-dimensional transducer arrays have transducer elements that are arranged in a non-rectangular, and preferably hexagonal grid. In a preferred embodiment, the transducer array has hexagonally shaped transducer elements. The transducer arrays may be fabricated as single or multiple layer structures. Selected transducer elements of the transducer array are coupled to an ultrasound imaging system that is used in medical diagnostic ultrasonic imaging applications.

Sparse transducer arrays may be fabricated in a hexagonal grid by connecting selected transducer elements to the imaging system. Also, the transducer array may comprise random, vernier and spiral arrays fabricated in a hexagonal grid.

The number of elements required to fully populate the hexagonal grid is 15% less then the number of elements required to fully populate a conventional rectangular grid. For example, a 110-element array in a hexagonal grid has the same grating lobe characteristics as a 128-element array in the conventional rectangular grid. As a result, the cost is reduced due to the fact that fewer processing channels are required.

Alternatively, the image quality is better in a hexagonal grid than in a conventional rectangular grid with the same number of processing channels. For example an aperture fully populated by using 128 elements in a hexagonal grid will have better grating lobe characteristics than an aperture fully populated by using 128 elements in a conventional rectangular grid.

Furthermore, a conventional rectangular grid has two axes of symmetry, compared to three in a hexagonal grid. As a result, grating lobes are distributed more symmetrically in the hexagonal grid than in the conventional rectangular grid, resulting in better grating lobe performance.

BRIEF DESCRIPTION OF SEVERAL VIEWS OF THE DRAWINGS

The various features and advantages of the present invention may be more understood with reference to the following detailed description taken in conjunction with the accompanying drawings wherein like reference numerals designate like structural elements, and in which:

FIG. 4 illustrates an exemplary ultrasound system in accordance with the principles of the present invention.

DETAILED DESCRIPTION OF THE INVENTION

Figure 1:
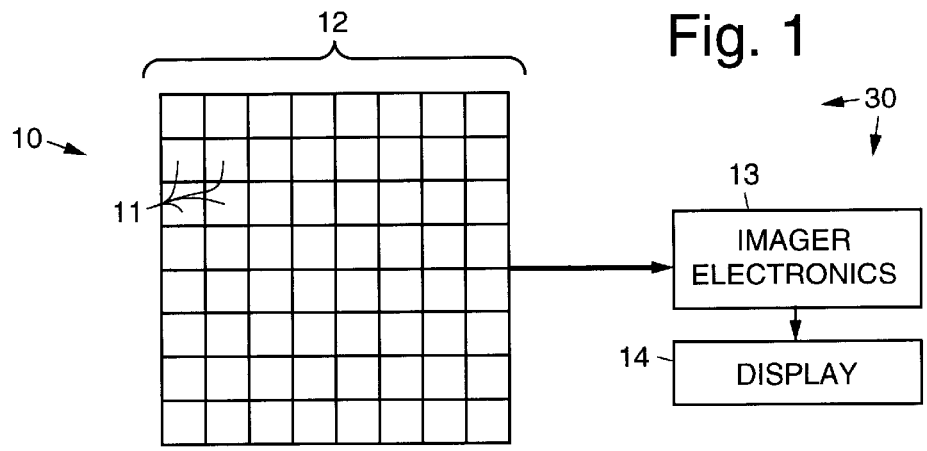
FIG. 1 illustrates a conventional two-dimensional array of transducer elements fabricated in a rectangular grid.

Referring to the drawing figures, FIG. 1 illustrates an ultrasound imaging system 30 comprising a conventional two-dimensional transducer array 10 having transducer elements 11 fabricated in a rectangular grid 12. In the case of a fully populated transducer array 10, all transducer elements 11 of the rectangular grid 12 are connected to imager electronics 13. The transducer array 10 is coupled by way of imager electronics 13 to a display 14 that displays an ultrasound image. In the case of a sparse array 10, only some of the transducer elements 11 of the rectangular grid 12 are connected to the ultrasound imaging system 13.

The conventional transducer array 10 is relatively costly because of the relatively high number of transducer elements 11 used in the array 10. Also, the transducer elements 11 of the conventional transducer array 10 are not arranged so as to maximize the two-dimensional symmetry of the point spread function so that the ultrasound imaging system 13 can produce symmetric speckle shapes.

Figure 2:
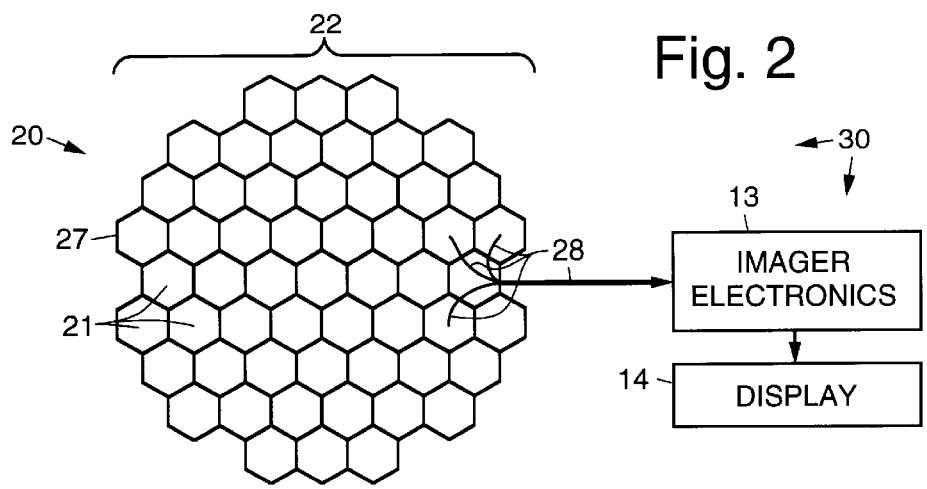
FIG. 2 illustrates an exemplary two-dimensional array of transducer elements in accordance with the principles of the present invention.

Referring to FIG. 2, it illustrates an ultrasound imaging system 30 comprising an exemplary two-dimensional non-rectangular or hexagonal grid transducer array 20 in accordance with the principles of the present invention. The improved transducer array 10 is coupled by way of imager electronics 13 to a display 14 that displays an ultrasound image. The two-dimensional transducer array 20 preferably comprises hexagonally shaped transducer elements 21 that are fabricated and arranged in a hexagonal grid 22 on a substrate 27.

However, it is to be understood that the grid 22 of the transducer array 20 is non-rectangular and is not necessarily hexagonally shaped. It is also to be understood that the shape of the transducer elements 21 is not limited only to a hexagonal one. The primary improvement provided by the present invention is the arrangement of transducer elements 21 in the non-rectangular or hexagonal grid 22.

The substrate 27 may comprise bulk silicon. The substrate 27 may also be selected from a group including bulk glass, sapphire, quartz, semiconductor or ceramic material. The transducer elements 21 may also comprise surface micromachinable films or bulk micromachinable elements, and include capacitively driven capacitive micromachined ultrasonic transducers, or otherwise acoustically excitable membranes. Acoustically excitable membranes may each be driven by a coupled piezofilm (PMUT), for example.

The two-dimensional transducer array 20 has selected ones of its hexagonally shaped transducer elements 21 electrically interconnected to an ultrasound system 13. Thus, a plurality of interconnections 28 (generally illustrated) is routed to the plurality of transducer elements 21. The two-dimensional transducer array 20 is preferably used in two-dimensional and three-dimensional medical diagnostic ultrasonic imaging applications. The two-dimensional transducer array 20 may be fabricated as single or multiple layer structure.

Because the two-dimensional array 20 has a hexagonal grid 22 of transducer elements 21, 15% fewer channels (electrical connections between the transducer elements 21 and the ultrasound imaging system 13) are required compared to the conventional rectangular grid 12 in the case of a fully populated array 20. Also, the two-dimensional hexagonal grid array 20 has better circular symmetry compared to conventional rectangular grid array 10. This provides for a two-dimensional array 20 that produces a more symmetric point spread function.

Arbitrary distributions of hexagonally shaped transducer elements 21, such as random, vernier and spiral, are more easily fabricated in the hexagonal grid 22 compared to the conventional rectangular grid 12 of transducer elements 11 because the hexagonal grid more closely approximates arbitrary distributions of elements than a rectangular grid. Also, energy lost in lateral modes of resonance in triangular piezoelectric transducer (PZT) posts 23 (FIG. 3) are generally smaller than the lateral modes of resonance in rectangular piezoelectric transducer posts of the conventional transducer array 10. Due to the hexagonal shape of the elements, element crosstalk is also minimized.

Figure 3:
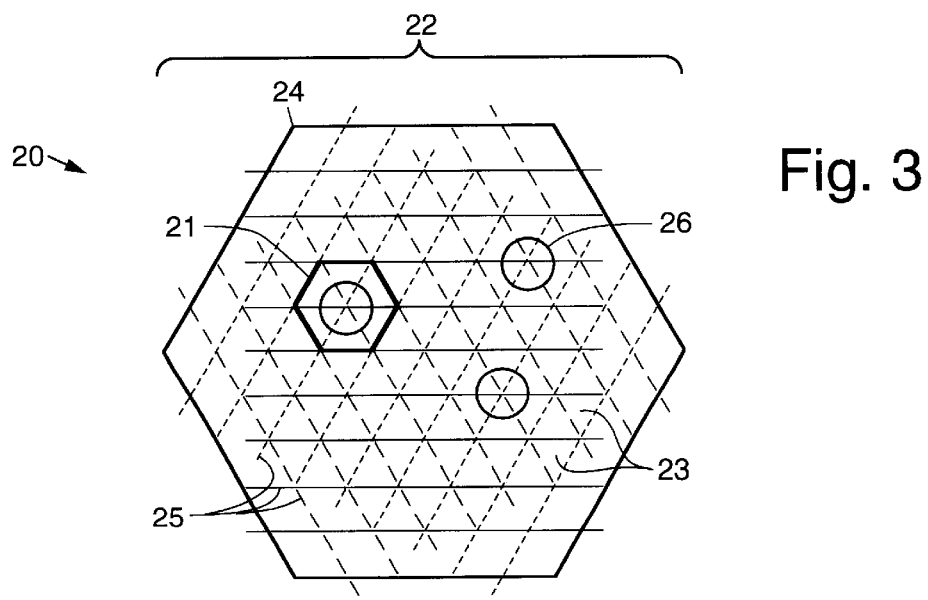
FIG. 3 illustrates an exemplary way to fabricate transducer elements in a hexagonal grid.

FIG. 3 illustrates an exemplary way to fabricate a two-dimensional transducer array 20 having transducer elements 21 arranged in a hexagonal grid 22. A piezoelectric transducer "blank" 24 (substrate 27) is diced in three different directions (illustrated by the three sets of parallel lines crossing the piezoelectric transducer blank 24), each angled 120° relative to each other, thus producing triangular posts 23. Six posts 23 are connected together by using bumps of a flex circuit (not shown) to form transducer elements 21 that are hexagonal in shape. This technique has been used to produce a reduced-to-practice proof of principle embodiment of the two-dimensional transducer array 20. The footprint of the transducer can be made hexagonal, circular, or any other shape by cropping the edges of the substrate. However, the preferable shape is circular.

The typical construction of a two-dimensional transducer array 20 having hexagonal transducer elements 21 involves dicing the piezoelectric transducer blank 24 deeper than the thickness of the final resonant thickness of the array 20, yet shallower than the thickness of the blank 24. This leaves an undiced spine on one side of the blank 24 that holds the triangular posts 23 in place. After the piezoelectric transducer blank 24 is fully diced and cleaned, kerfs 25 (illustrated by the three sets of parallel lines crossing the piezoelectric transducer blank 24) between the triangular posts 23 are filled with a typical kerf filler such as epoxy or urethane, for example. The filler is allowed to harden to produce a composite structure. The spine of the formed composite structure (piezoelectric transducer blank 24 plus filler) is ground or lapped away. Finally, the composite structure is ground or lapped to final thickness.

The triangular post composite structure forming the array 20 is fully plated with a metallic electrical conductor using techniques such as electroless plating, sputtering or other types of metal deposition, for example. If the composite structure forming the array 20 is given an electrode pattern deposition, the process is complete. If the composite structure forming the array 20 is completely plated, electrodes 26 may be generated using laser ablation or chemical masking and etching techniques, for example.

Quarterwave matching layers (not shown) may be applied to a patient side of the array 20 using known techniques including the application of a sacrificial mold to the face of the array, casting the quarterwave matching layer in a mold, allowing the quarterwave matching layer to harden, grinding the mold and quarterwave matching layer to thickness, and then washing (or heating) the sacrificial mold away. Many low melting temperature metals or polymers may be used for the sacrificial molds. Other techniques include laser machining of quarterwave matching layers into posts 23.

Other techniques for fabricating hexagonal elements include fabrication of capacitive micromachined ultrasonic transducer (cMUT) elements, laser drilling, and ceramic molding. Capacitive micromachined ultrasonic transducer (cMUT) elements are discussed in U.S. patent application Ser. No. 09/455,881, filed Dec. 6, 1999, and entitled "Micromachined Ultrasonic Spiral Arrays for Medical Diagnostic Imaging" assigned to the assignee of the present invention, for example. The contents of this application are incorporated by reference herein in its entirety.

Transducer arrays 20 having multiple-layer hexagonal grids 22 of transducer elements 11 may also be realized to produce the two-dimensional transducer array 20. The multiple-layer transducer arrays 20 may be fabricated using generally well known transducer array fabrication techniques. For example, U.S. Pat. No. 5,945,770 entitled "Multilayer Ultrasound Transducer and the Method of Manufacture Thereof" assigned to the assignee of the present invention discloses a typical multiple-layer transducer array that may be readily adapted to incorporate the non-rectangular or hexagonal grids 22 of transducer elements 11 in accordance with the principles of the present invention.

Referring now to FIG. 4, details of an exemplary ultrasound system 30 are generally shown that incorporates the non-rectangular or hexagonal grid transducer array 20 in accordance with the principles of the present invention. The ultrasound system 30 includes the transducer array 20 which is coupled by way of the imager electronics 13 to the display 14, which displays an ultrasound image.

The imager electronics 13 comprises a transmit beamformer 31 and a receive beamformer 32 coupled to the transducer array 20. A filter block 33, comprising a fundamental band filter 34 and harmonic band filter 35, is coupled to the receive beamformer 32. A signal processor 36, comprising a Doppler processor 37 and a B mode processor 38, is coupled to the filter block 33. Outputs of the fundamental filter 34 and harmonic filter 35 are each coupled to the Doppler processor 37 and the B mode processor 38. A scan converter 40 is coupled to outputs of the Doppler processor 37 and B mode processor 38. An image data storage 42 is coupled to a three-dimensional reconstruction computer 41, along with outputs of the scan converter 40. Optionally the transducer array 20, the Doppler processor 37, and the B mode processor 38 are coupled to the three-dimensional reconstruction computer 41, which generates a three-dimensional image. The display 14 is coupled to the three-dimensional reconstruction computer 41 for displaying a reconstructed ultrasound image.

The exemplary ultrasound system 30 is configurable to acquire information corresponding to a plurality of two-dimensional representations or image planes of a subject for generating a three-dimensional image. Alternatively, it can also acquire three-dimensional images directly by firing a multitude of ultrasound lines filling the three-dimensional space. Other systems, such as those for acquiring data with a two-dimensional, 1.5 dimensional or a single element transducer array, may be used. The transducer may be used to image the patient from the outside or from the inside by accessing the body through the esophagus, arteries, veins, or any other orifice. To generate three-dimensional representations of a subject during an imaging session, the ultrasound system 30 is configured to transmit, receive and process during a plurality of transmit events. Each transmit event corresponds to firing one or more ultrasound scan lines into the subject.

The transmit beamformer 31 is constructed in a manner known in the art, and may be a digital or analog based beamformer 31 capable of generating signals at different frequencies. The transmit beamformer 31 generates one or more excitation signals. Each excitation signal has an associated center frequency. As used herein, the center frequency represents the frequency in a band of frequencies approximately corresponding to the center of the amplitude distribution. Preferably, the center frequency of the excitation signals is within a 1 to 15 MHz range, such as 2 MHz, for example, and accounts for the frequency response of the transducer array 20. The excitation signals preferably have non-zero bandwidth.

Control signals are provided to the transmit beamformer 31 and the receive beamformer 32. The transmit beamformer 31 is caused to fire one or more acoustic lines in each transmit event, and the receive beamformer 32 is caused to generate in-phase and quadrature (I and Q) information along one or more scan lines. Alternatively, real value signals may be generated. A complete two-dimensional or three-dimensional data set (a plurality of scan lines) is preferably acquired before information for the next data set is acquired.

Upon the firing of one or more ultrasound scan lines into the subject, some of the acoustical energy is reflected back to the transducer array 20. In addition to receiving signals at the fundamental frequency (i.e., the same frequency as that transmitted), the nonlinear characteristics of tissue or optional contrast agents also produce responses at harmonic frequencies. Harmonic frequencies are frequencies associated with nonlinear propagation or scattering of transmit signals.

As used herein, harmonic includes subharmonics and fractional harmonics as well as second, third, fourth, and other higher harmonics. Fundamental frequencies are frequencies corresponding to linear propagation and scattering of the transmit signals of the first harmonic. Nonlinear propagation or scattering corresponds to shifting energy associated with a frequency or frequencies to another frequency or frequencies. The harmonic frequency band may overlap the fundamental frequency band.

The filter block 33 passes information associated with a desired frequency band, such as the fundamental band using fundamental band filter 34 or a harmonic frequency band using the harmonic band filter 35. The filter block 33 may be included as part of the receive beamformer 32. Furthermore, the fundamental band filter 34 and the harmonic band filter 35 preferably comprise one filter that is programmable to pass different frequency bands, such as the fundamental, second or third harmonic bands.

For example, the filter block 33 demodulates the summed signals to baseband. The demodulation frequency is selected in response to the fundamental center frequency or another frequency, such as a second harmonic center frequency. For example, the transmitted ultrasonic waveforms are transmitted at a 2 MHz center frequency. The summed signals are then demodulated by shifting by either the fundamental 2 MHz or the second harmonic 4 MHz center frequencies to baseband (the demodulation frequency). Other center frequencies may be used.

Signals associated with frequencies other than near baseband are removed by low pass filtering. As an alternative or in addition to demodulation, the filter block 33 provides band pass filtering. The signals are demodulated to an intermediate frequency (IF) ( e.g., 2 MHz) or not demodulated and a band pass filter is used. Thus, signals associated with frequencies other than a range of frequencies centered around the desired frequency or an intermediate frequency) are filtered from the summed signals. The demodulated or filtered signal is passed to the signal processor 36 as the complex I and Q signal, but other types of signals, such as real value signals, may be passed.

By selectively filtering which frequencies are received and processed, the ultrasound system 30 produces images with varying characteristics. In tissue harmonic imaging, no additional contrast agent is added to the target, and only the nonlinear characteristics of the tissue are relied on to create the ultrasonic image. Medical ultrasound imaging is typically conducted in a discrete imaging session for a given subject at a given time. For example, an imaging session can be limited to a patient examination of a specific tissue of interest over a period of ¼ to 1 hour, although other durations are possible. In this case, no contrast agent is introduced into the tissue at any time during the imaging session.

Tissue harmonic images provide a particularly high spatial resolution and often possess improved contrast resolution characteristics. In particular, there is often less clutter in the near field. Additionally, because the transmit beam is generated using the fundamental frequency, the transmit beam profile is less distorted by a specific level of tissue-related phase aberration than a profile of a transmit beam formed using signals transmitted directly at the second harmonic.

The harmonic imaging technique described above may be used for both tissue and contrast agent harmonic imaging. In contrast agent harmonic imaging, any one of a number of well known nonlinear ultrasound contrast agents, such as micro-spheres or an FS069 agent by Schering of Germany, are added to the target or subject in order to enhance the nonlinear response of the tissue or fluid. The contrast agents radiate ultrasonic energy at harmonics of an insonifying energy at fundamental frequencies.

The signal processor 36 comprises one or more processors for generating two-dimensional Doppler or B-mode information. For example, a B-mode image, a color Doppler velocity image (CDV), a color Doppler energy image (CDE), a Doppler tissue image (DTI), a color Doppler variance image, or combinations thereof may be selected by a user. The signal processor 36 detects the appropriate information for the selected image.

Preferably, the signal processor 36 comprises a Doppler processor 37 and a B-mode processor 38. Each of the processors, 37, 38 is preferably a digital signal processor and operates as known in the art to detect information. As is known in the art, the Doppler processor 37 estimates velocity, variance of velocity and energy from the I and Q signals. As known in the art, the B-mode processor 38 generates information representing the intensity of the echo signal associated with the I and Q signals.

The information generated by the signal processor 36 is provided to the scan converter 40. Alternatively, the scan converter 40 includes detection steps as is known in the art and described in U.S. Pat. No. 5,793,701, issued Aug. 11, 1998, entitled "Method and apparatus for coherent image formation" assigned to the assignee of the present invention. The scan converter 40 is constructed in a manner known in the art to arrange the output of the signal processor 36 into two- or three-dimensional representations of image data. Preferably, the scan converter 40 outputs formatted video image data frames, using a format such as the DICOM medical industry image standard format or a TIFF format.

Thus, the two- or three-dimensional representations are generated. Each of the representations corresponds to a receive center frequency, such as a second harmonic center frequency, a type of imaging, such as B-mode, and positional information. The harmonic based representations may have better resolution and less clutter than fundamental images. By suppressing the harmonic content of the excitation signal, the benefits of harmonic imaging of tissue may be increased.

The plurality of two- or three-dimensional representations of the subject is stored in the image data storage 42. The three-dimensional reconstruction computer 41 operates on the stored plurality of two- or three-dimensional representations and assembles them into a three-dimensional representation. Alternatively, the three-dimensional reconstruction computer 41 may also input pre-scan converted acoustic data to convert to three-dimensional data sets as well. The completed three-dimensional reconstruction is then displayed on the display 14.

Thus, improved two-dimensional ultrasonic transducer arrays having transducer elements arranged in a non-rectangular or hexagonal grid and ultrasound imaging systems employing same have been disclosed. It is to be understood that the described embodiments are merely illustrative of some of the many specific embodiments that represent applications of the principles of the present invention. Clearly, numerous and other arrangements can be readily devised by those skilled in the art without departing from the scope of the invention.

What is claimed is:

1. A medical diagnostic ultrasonic transducer array comprising:
   a substrate having a plurality of transducer elements disposed in a non-rectangular grid on the substrate; and
   a plurality of interconnections routed to the plurality of transducer elements;
   wherein selected ones of the transducer elements that characterize an arbitrary distribution pattern are electrically interconnected to an ultrasound system.

2. The transducer array recited in claim 1 wherein the non-rectangular grid of transducer elements is hexagonal.

3. The transducer array recited in claim 2 wherein selected ones of the transducer elements that characterize a sparse transducer element pattern are electrically interconnected to an ultrasound system.

4. The transducer array recited in claim 2 wherein the transducer elements each have a hexagonal shape.

5. The transducer array recited in claim 2 wherein selected ones of the transducer elements are electrically interconnected to an ultrasound system.

6. The transducer array recited in claim 2 further comprising a plurality of interconnected substrates that form a multiple layer transducer array.

7. The transducer array recited in claim 2 wherein all of the transducer elements are electrically interconnected to an ultrasound system.

8. The transducer array recited in claim 2 wherein randomly selected ones of the transducer elements are electrically interconnected to an ultrasound system.

9. The transducer array recited in claim 2 wherein selected ones of the transducer elements that characterize a vernier transducer element pattern are electrically interconnected to an ultrasound system.

10. The transducer array recited in claim 2 wherein selected ones of the transducer elements that characterize a spiral transducer element pattern are electrically interconnected to an ultrasound system.

11. The transducer array recited in claim 1 wherein the transducer elements each have a hexagonal shape.

12. The transducer array recited in claim 1 wherein selected ones of the transducer elements are electrically interconnected to an ultrasound system.

13. A medical diagnostic ultrasonic transducer array comprising:
   a substrate having a plurality of transducer elements disposed in a non-rectangular grid on the substrate;
   a plurality of interconnections routed to the plurality of transducer elements; and
   a plurality of interconnected substrates that form multiple layers of transducers.

14. The transducer array recited in claim 1 wherein all of the transducer elements are electrically interconnected to an ultrasound system.

15. The transducer array recited in claim 1 wherein randomly selected ones of the transducer elements are electrically interconnected to an ultrasound system.

16. The transducer array recited in claim 1 wherein selected ones of the transducer elements that characterize a vernier transducer element pattern are electrically interconnected to an ultrasound system.

17. The transducer array recited in claim 1 wherein selected ones of the transducer elements that characterize a spiral transducer element pattern are electrically interconnected to an ultrasound system.

18. A medical diagnostic ultrasound imaging system comprising:
   a transducer array including a substrate having a plurality of transducer elements disposed in a non-rectangular grid on the substrate, and a plurality of interconnections routed to the plurality of transducer elements;
   a transmit beamformer coupled to the transducer array;
   imager electronics electrically coupled to the plurality of plurality of interconnections of the transducer array for generating an ultrasound image; and
   a display coupled to the imager electronics for displaying an ultrasound image.

19. The imaging system recited in claim 18 wherein the non-rectangular grid of transducer elements is hexagonal.

20. The imaging system recited in claim 18 wherein the imager electronics comprises:
   a receive beamformer coupled to the transducer array;
   a filter block, comprising a fundamental band filter and harmonic band filter, coupled to the receive beamformer;
   a signal processor, comprising a Doppler processor and a B mode processor, coupled to the filter block;
   a scan converter coupled to outputs of the Doppler processor and B mode processor;
   a three-dimensional reconstruction computer coupled to the scan converter; and an image data storage coupled to the three-dimensional reconstruction computer.

21. The imaging system recited in claim 20 wherein the transducer array, the Doppler processor, and the B mode processor are coupled to the three-dimensional reconstruction computer, which receives data therefrom and reconstructs a three-dimensional image.

22. A method of fabricating a two-dimensional medical diagnostic ultrasonic transducer array comprising the steps of:
   dicing a piezoelectric transducer substrate in three directions angled 120 degrees relative to each other to produce triangular posts; and
   connecting six posts together using bumps of a flex circuit to form transducer elements that are hexagonal in shape.

* * * * *